US010435348B2

(12) United States Patent
Kong et al.

(10) Patent No.: US 10,435,348 B2
(45) Date of Patent: Oct. 8, 2019

(54) PROCESS FOR PRODUCING AROMATICS, P-XYLENE AND TEREPHTHALIC ACID, AND DEVICE FOR PRODUCING AROMATICS

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Dejin Kong, Shanghai (CN); Junlin Zheng, Shanghai (CN); Qi Song, Shanghai (CN); Xiaolan Qi, Shanghai (CN); Xuan Xu, Shanghai (CN); Xiangdong Jiang, Shanghai (CN); Deqin Yang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 15/737,976

(22) PCT Filed: Jun. 17, 2016

(86) PCT No.: PCT/CN2016/000314
§ 371 (c)(1),
(2) Date: Dec. 19, 2017

(87) PCT Pub. No.: WO2016/201954
PCT Pub. Date: Dec. 22, 2016

(65) Prior Publication Data
US 2018/0282256 A1 Oct. 4, 2018

(30) Foreign Application Priority Data

Jun. 19, 2015 (CN) .......................... 2015 1 0344799

(51) Int. Cl.
C07C 63/26 (2006.01)
C07C 2/08 (2006.01)
C07C 2/12 (2006.01)
C07C 1/207 (2006.01)
C07C 5/42 (2006.01)
C12P 5/02 (2006.01)
B01J 37/04 (2006.01)
B01J 21/04 (2006.01)
B01J 29/04 (2006.01)
B01J 29/40 (2006.01)
B01J 29/44 (2006.01)
(Continued)

(52) U.S. Cl.
CPC ............... C07C 63/26 (2013.01); B01J 21/04 (2013.01); B01J 29/041 (2013.01); B01J 29/405 (2013.01); B01J 29/44 (2013.01); B01J 29/46 (2013.01); B01J 29/60 (2013.01); B01J 29/7007 (2013.01); B01J 29/7038 (2013.01); B01J 29/7046 (2013.01); B01J 29/80 (2013.01); B01J 37/0018 (2013.01); B01J 37/04 (2013.01); C07C 1/2078 (2013.01); C07C 2/08 (2013.01); C07C 2/12 (2013.01); C07C 5/42 (2013.01); C07C 15/08 (2013.01); C07D 307/33 (2013.01); C12P 5/02 (2013.01); C07C 2521/06 (2013.01); C07C 2529/076 (2013.01); C07C 2529/40 (2013.01); C07C 2529/70 (2013.01); C10G 2300/1011 (2013.01); Y02P 20/52 (2015.11); Y02P 30/20 (2015.11)

(58) Field of Classification Search
CPC ......... C07C 63/26; C07C 1/2078; C07C 2/08; C07C 15/08
See application file for complete search history.

(56) References Cited

U.S. PATENT DOCUMENTS 2,438,041 A * 3/1948 Dutcher .................... C07C 2/50
585/322
4,792,620 A * 12/1988 Paulik .................. B01J 31/0231
560/232
(Continued)

FOREIGN PATENT DOCUMENTS

CN 1393425 A 1/2003
CN 101890373 A 11/2010
(Continued)

OTHER PUBLICATIONS

Xia et al, Journal of Fuel Chemistry and Technology, Catalytic conversion of biomass derivative g-valerolactone to aromatics over Zn/ZSM-5 catalyst, 2015, 43(5), pp. 575-580. (Year: 2015).*
(Continued)

Primary Examiner — Paul A Zucker
(74) Attorney, Agent, or Firm — Novik, Kim & Lee, PLLC; Allen Xue

(57) ABSTRACT

The present invention relates to a process for producing aromatics, a process for producing p-xylene and terephthalic acid, and a device for producing aromatics. The process for producing aromatics at least comprises a step of producing C8 olefin from a compound having a lactone group and a step of producing aromatics from the C8 olefin. The process for producing aromatics has the characters of high yield of aromatics and high selectivity to xylene.

26 Claims, No Drawings

(51) Int. Cl.
  *B01J 29/46* (2006.01)
  *B01J 29/60* (2006.01)
  *B01J 29/70* (2006.01)
  *B01J 29/80* (2006.01)
  *B01J 37/00* (2006.01)
  *C07C 15/08* (2006.01)
  *C07D 307/33* (2006.01)

(56) References Cited

U.S. PATENT DOCUMENTS

2009/0227823 A1  9/2009  Huber et al.
2011/0257416 A1  10/2011  Cortright et al.

FOREIGN PATENT DOCUMENTS

CN  2011149559 A2  12/2011
CN  2012015541 A2  2/2012

OTHER PUBLICATIONS

Norskov et al, Nature Chemistry, Towards the Computational Design of Solid Catalysts, 2009, 1, pp. 37-46. (Year: 2009).*
Zaragoza Dorwald, Side Reactions in Organic Synthesis, 2005, Wiley-VCH Verlag GmbH & Co. KGaA, Weinheim, Preface. p. IX ) (Year: 2005).*
Bond et al, Science, Integrated Catalytic Conversion of g-Valerolactone to Liquid Alkenes for Transportation Fuels, Feb. 26, 2010, 327, pp. 1110-1114. (Year: 2010).*
Tomas et al, Chemical Reviews, p-Xylene Oxidation to Terephthalic Acid: A Literature Review Oriented toward Process Optimization and Development, 2013, 113, pp. 7421-7469. (Year: 2013).*
Katherine Bourzac, "A startup's catalytic process converts biomass directly into components of gasoline", MIT Technology Review, Mar. 29, 2010.
David Martin Alonso et al., "Direct conversion of cellulose to levulinic acid and gamma-valerolactone using solid acid catalysts", Catalysis Science & Technology, 2013,3, pp. 927-931.
Stephanie G. Wettstein et al., "Production of levulinic acid and gamma-valerolactone (GVL) from cellulose using GVL as a solvent in biphasic systems", Energy Environmental Science, 2012, 5, pp. 8199-8203.
Yosuke Muranaka et al., "Effective Production of Levulinic Acid from Biomass through Pretreatment Using Phosphoric Acid, Hydrochloric Acid, or Ionic Liquid", Industrial & Engineering Chemistry Resarch, 2014, 53 (29), pp. 11611-11621.
Yun Ma, "Advances in SO2-4/MxOy solid superacid catalysts", Applied Chemical Industry, vol. 43, No. 10, Oct. 2014, pp. 1879-1890.
European Patent Office, Supplementary European Search Report for EP 16810695, dated Jan. 8, 2019.

* cited by examiner

PROCESS FOR PRODUCING AROMATICS, P-XYLENE AND TEREPHTHALIC ACID, AND DEVICE FOR PRODUCING AROMATICS

TECHNICAL FIELD

The present invention relates to a process for producing aromatics, in particular to a process for producing an aromatic product rich in xylene. The present invention further relates to a process for producing p-xylene (sometimes called as PX hereinafter) and terephthalic acid based on the process for producing aromatics, and to a device for producing the aromatics.

BACKGROUND

Aromatics are important basic raw materials for petrochemical industry, widely useful for polyester, chemical fiber, rubber and the like fields. Benzene, toluene, and xylene are the most widely used three aromatics, wherein PX is mostly demanded and has the widest use. Currently, the production of aromatics in the world depends predominantly on the non-renewable fossil resource, whilst due to the limited reserves and non-renewability of the fossil resource, the cost for producing aromatics is increasing. In addition, the continual exploitation and utilization of the fossil resource results in significant discharge of greenhouse gases, leading to more and more serious environmental problems. Therefore, it is of significant importance to develop a process of producing aromatics (especially xylene) from renewable resources.

As a renewable resource, it is now interested in producing aromatics (especially xylene) using biomass as a raw material. There are reports in the prior art about converting biomass into aromatics, and also about platform compounds therefor (see, e.g., Katherine Bourzac, From biomass to chemicals In one step, MIT Technology Review, 2010-03-29; US20090227823 and US20110257416A1).

However, these prior arts have a general disadvantage of a relatively low carbon availability during the conversion from biomass to aromatics, resulting in a relatively low yield of aromatics too. In addition, these prior arts have another general disadvantage of relatively low proportion of xylene (e.g., PX) in the aromatics obtained using the platform compound from prior art to produce aromatics, resulting in increased operation cost and operation complexity of the subsequent separation and purification steps for providing PX product in a high purity.

SUMMARY OF THE INVENTION

Regarding the situations in the prior art introduced above, the inventors of the present invention deem it desirable to develop a process for producing aromatics demonstrating improved carbon availability and in turn achieving improved aromatics yield, compared with the processes for producing aromatics of prior art, during the conversion from biomass to aromatics. Further, the inventors of the present invention also deem it desirable to develop a process for producing aromatics resulting in increased proportion of xylene in the aromatic product obtained, compared with the processes for producing aromatics of prior art, so as to produce an aromatic product rich in xylene.

The inventors of the present invention have discovered through hard study that the problems present in the prior art above can be solved by using a specific compound having a lactone group as a platform compound through reaction steps in a specific sequence, and thus have achieved the present invention.

Specifically, the present invention involves the following aspects of contents.

1. A process for producing aromatics, comprising the steps of a1) and b1) or comprising the steps of a2), b2) and c2):

a1) a step of contacting a compound having a lactone group with a decarboxylation and dimerisation catalyst, under conditions for decarboxylation and dimerisation reaction, to produce a C8 olefin; and b1) a step of contacting the C8 olefin with an aromatization catalyst under aromatization reaction conditions, to produce aromatics, or a2) a step of contacting a compound having a lactone group with a decarboxylation catalyst, under decarboxylation reaction conditions, to produce a C4 olefin; and b2) a step of contacting the C4 olefin with a dimerisation catalyst, under dimerization reaction conditions, to produce a C8 olefin; and c2) a step of contacting the C8 olefin with an aromatization catalyst under aromatization reaction conditions, to produce aromatics, wherein, the compound having a lactone group has the structural formula (I):

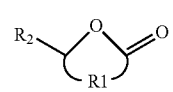

(I)

in formula (I), $R_1$ is selected from the group consisting of optionally substituted $C_{1-20}$ linear or branched alkylene, optionally substituted $C_{2-20}$ linear or branched alkenylene, optionally substituted $C_{2-20}$ linear or branched alkynylene, optionally substituted $C_{3-20}$ cycloalkylene and optionally substituted $C_{6-20}$ arylidene, preferably selected from the group consisting of optionally substituted $C_{2-10}$ linear or branched alkylene and optionally substituted $C_{2-10}$ linear or branched alkenylene, more preferably $C_{2-5}$ linear or branched alkylene, further preferably 1,2-ethylidene; and $R_2$ is selected from the group consisting of hydrogen, optionally substituted $C_{1-20}$ linear or branched alkyl and carboxyl, preferably selected from the group consisting of hydrogen and optionally substituted $C_{1-10}$ linear or branched alkyl, more preferably selected from the group consisting of hydrogen and $C_{1-4}$ linear or branched alkyl.

2. The process according to any one of the preceding aspects, wherein the conditions for the decarboxylation and dimerization reaction comprise: a reaction temperature of 160 to 400 degree Celsius, preferably 160 to 300 degree Celsius, a reaction pressure of 0.1 to 8 MPa, preferably 0.1 to 4 MPa, a weight hourly space velocity (WHSV) for the compound having a lactone group of 0.1 to 15 hour$^{-1}$, preferably 0.6 to 5 hour$^{-1}$; or alternatively, the conditions for the decarboxylation reaction comprise: a reaction temperature of 100 to 350 degree Celsius, preferably 120 to 250 degree Celsius, a reaction pressure of 0.1 to 8 MPa, preferably 0.1 to 4 MPa, a WHSV for the compound having a lactone group of 0.1 to 15 hour$^{-1}$, preferably 0.6 to 5 hour$^{-1}$; or alternatively, the conditions for the dimerization reaction comprise: a reaction temperature of 160 to 400 degree Celsius, preferably 160 to 300 degree Celsius, a reaction pressure of 0.1 to 8 MPa, preferably 0.1 to 4 MPa, a WHSV for the C4 olefin of 0.1 to 15 hour$^{-1}$, preferably 0.6 to 5 hour$^{-1}$; or alternatively, the conditions for the aromatization reaction comprise: a reaction temperature of 420 to 800 degree Celsius, preferably 450 to 550 degree Celsius, a reaction pressure of 0.1 to 8 MPa, preferably 0.1 to 4 MPa, a WHSV for the C8 olefin of 0.3 to 10 hour$^{-1}$, preferably 0.3 to 5 hour$^{-1}$.

3. The process according to any one of the preceding aspects, wherein the compound having a lactone group is derived from a biomass material, preferably derived from one or more of xylitol, glucose, cellobiose, cellulose, hemicellulose and lignin, or derived from one or more of paper manufacture sludge, waste paper, bagasse, glucose, wood, corn cob, corn stover and straw stover.

4. The process according to any one of the preceding aspects, wherein the decarboxylation and dimerisation catalyst is one or more selected from the group consisting of acidic oxide, oxide of bismuth, strongly acidic cation exchange resin, molecular sieve, solid superacid and composite metal oxide; the decarboxylation catalyst is one or more selected from the group consisting of acidic oxide, strongly acidic cation exchange resin, molecular sieve, solid superacid and composite metal oxide, preferably one or more selected from the group consisting of acidic oxide, strongly acidic cation exchange resin and solid superacid, more preferably one or more selected from the group consisting of strongly acidic cation exchange resin and solid superacid; the dimerisation catalyst is one or more selected from the group consisting of acidic oxide, oxide of bismuth, strongly acidic cation exchange resin, molecular sieve, solid superacid and composite metal oxide, preferably molecular sieve; the aromatization catalyst is one or more selected from the group consisting of molecular sieve, solid superacid and composite metal oxide, preferably molecular sieve, in particular ZSM-5 or M/ZSM-5, wherein M is selected from the group consisting of Zn, Ga, Sn or a combination thereof.

5. The process according to any one of the preceding aspects, wherein the acidic oxide is one or more selected from the group consisting of solid oxide of an element from Group IIIA of the periodic table of elements and solid oxide of an element from Group IVA of the periodic table of elements, preferably one or more selected from the group consisting of $SiO_2$ and $Al_2O_3$, more preferably $Al_2O_3$, $Al_2O_3$—$SiO_2$ $SiO_2$, the oxide of bismuth is $Bi_2O_3$, the strongly acidic cation exchange resin is one or more selected from the group consisting of macroporous sulfonic acidic cation exchange resin and halogen modified (preferably perfluorinated) sulfonic acidic cation exchange resin, more preferably one or more selected from the group consisting of Amberlyst® series resins and Nafion® series resins.

6. The process according to any one of the preceding aspects, wherein the acidity D1 of the decarboxylation and dimerisation catalyst and the acidity D2 of the aromatization catalyst satisfy the following formula (I), $$D1 > D2 \qquad (I)$$

or alternatively, the acidity D11 of the decarboxylation catalyst, the acidity D12 of the dimerisation catalyst and the acidity D2 of the aromatization catalyst satisfy the following formula (II), $$D11 > D2 > D12 \qquad (II)$$

7. The process according to any one of the preceding aspects, wherein the molecular sieve is one or more selected from the group consisting of ZSM-type molecular sieve (preferably one or more selected from the group consisting of ZSM-5, ZSM-11, ZSM-22, ZSM-23 and ZSM-38), Y-type molecular sieve, beta-type molecular sieve, L-type molecular sieve, MCM-type molecular sieve (preferably one or more selected from the group consisting of MCM-22 and MCM-41), preferably one or more selected from the group consisting of ZSM-5, Y-type molecular sieve, beta-type molecular sieve and MCM-41, more preferably ZSM-5.

8. The process according to any one of the preceding aspects, wherein the molecular sieve is a molecular sieve composition, comprising the following components of a1), b1) and c1) or comprising the following components of a2) and c2:

a1) 20 to 80 parts by weight (preferably 50 to 80 parts by weight) of the molecular sieve, and b1) 20 to 80 parts by weight (preferably 20 to 50 parts by weight) of a binder (preferably one or more selected from the group consisting of silica sol, pseudo-boehmite, alumina, acid treated clay, kaolin, montmorillonite, and bentonite, more preferably one or more selected from the group consisting of alumina, pseudo-boehmite and montmorillonite), and c1) 0 to 10 parts by weight (preferably 0.01 to 10 parts by weight, more preferably 0.01 to 5 parts by weight) of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, preferably one or more selected from the group consisting of Ca, K, Mg, Cr, Mo, Fe, Ni, Cu, Zn, Ga, Ru, Pd, Pt, Ag, B, Sn, P, La and Ce, more preferably one or more selected from the group consisting of Zn, Ga and Sn, or a2) 90 to 99.99 parts by weight (preferably 95 to 99.99 parts by weight) of the molecular sieve, and c2) 0.01 to 10 parts by weight (preferably 0.01 to 5 parts by weight) of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, preferably one or more selected from the group consisting of Ca, K, Mg, Cr, Mo, Fe, Ni, Cu, Zn, Ga, Ru, Pd, Pt, Ag, B, Sn, P, La and Ce, more preferably one or more selected from the group consisting of Zn, Ga and Sn.

9. The process according to any one of the preceding aspects, wherein in step a1), the compound having a lactone group is contacted with catalyst bed layers containing the decarboxylation and dimerisation catalyst to produce a C8 olefin, the catalyst bed layers comprising at least two layers of the decarboxylation and dimerisation catalyst, wherein the acidities of any two adjacent layers of the decarboxylation and dimerisation catalysts are different.

10. The process according to any one of the preceding aspects, wherein the solid superacid is one or more selected from the group consisting of supported Lewis acid solid superacid, solid as inorganic metal salt/Lewis acid composite superacid and solid sulfated metal oxide superacid.

11. The process according to any one of the preceding aspects, wherein the support of the supported Lewis acid solid superacid is one or more of selected from the group consisting of solid oxide of an element from Group IIIA and solid oxide of an element from Group IVA of the periodic table of elements, preferably one or more of selected from the group consisting of $SiO_2$, $B_2O_3$ and $Al_2O_3$, the Lewis acid of the supported Lewis acid solid superacid is one or more selected from the group consisting of halide (preferably fluoride) of an element from Group VB, halide (preferably fluoride) of an element from Group IIIA and halide (preferably fluoride) of an element from Group VA of the periodic table of elements, preferably one or more selected from the group consisting of halide (preferably fluoride) of an element from Group VB and halide (preferably fluoride) of an element from Group VA of the periodic table of elements, further preferably one or more selected from the group consisting of $PF_3$, $AsF_3$, $SbF_3$, $BiF_3$, $SbF_5$, $TaF_3$, $VF_3$ and $NbF_3$, the supported Lewis acid solid superacid is preferably one or more selected from the group consisting of $SBF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$ and $NbF_3/Al_2O_3$—$B_2O_3$, the inorganic metal salt of the solid inorganic metal salt/Lewis acid composite superacid is one or more selected from the group consisting of inorganic acid salt (preferably haloid acid salt, more preferably hydrochloride) of a metal element from Group IB, inorganic acid salt (preferably haloid acid salt, more preferably hydrochloride) of a metal element from Group IIB, inorganic acid salt (preferably haloid acid salt, more preferably hydrochloride) of a metal element from Group VII and inorganic acid salt (preferably haloid acid salt, more preferably hydrochloride) of a metal element from Group VIII of the periodic table of elements, preferably $CuCl_2$, the Lewis acid of the solid inorganic metal salt/Lewis acid composite superacid is one or more selected from the group consisting of halide (preferably chloride) of an element from Group VB of the periodic table of elements, halide (preferably chloride) of an element from Group IIIA and halide (preferably chloride) of an element from Group VA, preferably one or more selected from the group consisting of halide (preferably chloride) of an element from Group IIIA of the periodic table of elements, preferably $AlCl_3$, the solid inorganic metal salt/Lewis acid composite superacid is preferably $AlCl_3$—$CuCl_2$, the metal oxide of the solid sulfated metal oxide superacid is oxide A of a metal element from Group IVB of the periodic table of elements (preferably one or more selected from the group consisting of $ZrO_2$ and $TiO_2$) or is oxide B obtained by modifying the oxide A with one or more modifying elements selected from the group consisting of metal element from Group IIIA (in the form of oxide), metal element from Group VIIB (in the form of oxide), noble metal element from Group VIII (in the form of metal elementary substance), base metal element from Group VIII (in the form of oxide), metal element from Group VIB (in the form of oxide) and lanthanide metal element (in the form of oxide) of the periodic table of elements (the modifying element being preferably one or more selected from the group consisting of Fe, Pt, Re, Al, W, Cr, Mo and Mn), the solid sulfated metal oxide superacid is preferably one or more selected from the group consisting of $SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$, $SO_4^{2-}/ZrO_2$—$Fe_2O_3$—$MnO_2$, W modified $SO_4^{2-}/Al_2O_3$—$ZrO_2$, and Mo modified $SO_4^{2-}/Al_2O_3$—$ZrO_2$.

12. The process according to any one of the preceding aspects, wherein in the supported Lewis acid solid superacid, the Lewis acid is supported in an amount of 1 to 30 wt %, preferably 1 to 15 wt %, relative to the weight of the support.

in the solid inorganic metal salt/Lewis acid composite superacid, the weight ratio between the inorganic metal salt and the Lewis acid is 1-30:100, preferably 1-15:100, in the solid sulfated metal oxide superacid, the metal oxide has a sulfated rate of 0.5-25 wt %, preferably 1-8 wt %, in the oxide B, the weight ratio of the modifying element in the form of oxide (calculated as oxide) to the oxide A is 0.1-25:100, preferably 0.5-10:100, and the weight ratio of the modifying element in the form of metal elementary substance (calculated as metal) to the oxide A is 0.1-15:100, preferably 0.3-6:100.

13. The process according to any one of the preceding aspects, wherein the composite metal oxide is a composite oxide of oxide C of a metal element from Group IVB of the periodic table of elements (preferably one or more selected from the group consisting of $ZrO_2$ and $TiO_2$, more preferably $ZrO_2$) and one or more oxides D selected from the group consisting of oxide of a metal element from Group IIIA, oxide of a metal element from Group VII, oxide of a metal element from Group VIB and lanthanide metal element of the periodic table of elements (preferably one or more selected from the group consisting of $B_2O_3$, $Al_2O_3$, $MnO_2$, $Cr_2O_3$, $CrO_3$, $MoO_3$, $WO_3$, $La_2O_3$ and $CeO_2$, more preferably one or more selected from the group consisting of $MnO_2$, $MoO_3$, $WO_3$, $La_2O_3$ and $CeO_2$), preferably a composite oxide of $ZrO_2$ and one or more oxides D selected from the group consisting of $MnO_2$, $Mo_2O_3$, $WO_3$, $La_2O_3$ and $CeO_2$.

14. The process according to any one of the preceding aspects, wherein the ratio of oxide C to oxide D is 60-99.9:0.1-40, preferably 60-99:1-40, calculated in parts by weight.

15. The process according to any one of the preceding aspects, further comprising a step of catalytic conversion of the biomass material, optionally followed by catalytic hydrogenation, so as to produce the compound having a lactone group.

16. A process for producing p-xylene, comprising the steps of: a step of producing aromatics according to any one of the preceding aspects; and a step of separating p-xylene from the aromatics. 17. A process for producing terephthalic acid, comprising the steps of:

a step of producing p-xylene according to any one of the preceding aspects; and a step of converting the p-xylene into terephthalic acid.

18. A device for producing aromatics, comprising the units of:

a decarboxylation and dimerisation unit, constructed as being capable of contacting a compound having a lactone group with a decarboxylation and dimerisation catalyst, under conditions for decarboxylation and dimerization reaction, to produce a C8 olefin; and an aromatization unit, constructed as being capable of contacting the C8 olefin with an aromatization catalyst under aromatization reaction conditions, to produce aromatics, optionally, the device further comprising a catalytic conversion unit, or a combination of a catalytic conversion unit with a catalytic hydrogenation unit:

the catalytic conversion unit being constructed as allowing catalytic conversion of the biomass material to generate a product comprising the compound having a lactone group;

the catalytic hydrogenation unit being constructed as being capable of increasing the proportion of the compound having a lactone group in the product through catalytically hydrogenating the product.

TECHNICAL EFFECT

According to one embodiment, the process for producing aromatics according to the present invention can, e.g., during the conversion process from biomass to aromatics, increase the carbon availability, reduce the proportion of carbon in the biomass material converted into gaseous carbon and carbon deposition, increase the yield of aromatics and finally increase the yield of xylene. For example, the yield of carbon as xylene can be up to 86.5%, preferably 60% or more, using the process for producing aromatics according to the present invention.

According to one embodiment, the process for producing aromatics according to the present invention, by using a specific compound having a lactone group as a platform compound in combination with reaction steps in a specific sequence, can increase significantly the conversion of the platform compound as compared with prior art, and can concurrently increase the selectivity to xylene significantly. For example, the process for producing aromatics according to the present invention can result in a conversion of the platform compound up to 99% or more, and a selectivity to xylene up to 94% or more.

According to one embodiment, compared with prior art, the process for producing aromatics according to the present invention can increase significantly the service life of the catalyst, and can in particular delay coking of the catalyst significantly.

According to one embodiment, compared with prior art, the process for producing aromatics according to the present invention can result directly in an aromatic product with significantly more enriched xylene, wherein the content of xylene in the aromatic product is generally greater than 30 wt %, preferably 50 wt % or more, more preferably 70 wt % or more.

EMBODIMENTS

The embodiments of the present invention are illustrated below, whilst it should be understood that the protection scopes of the present invention are not restricted thereto; instead, the protection scopes are defined by the claims attached.

The publications, patent applications, patents and other references cited in the specification are all incorporated herein by reference. Unless otherwise defined, the scientific and technical terms used in the specification have meanings same as those conventionally known by those skilled in the art. In case of any confliction occurs, including any definitions, those skilled should understand referring to the present specification.

When the specification describes material, process, part, device or equipment modified with terms of "known by those skilled in the art" or "conventionally known in the art" or the like, the terms should be understood not only according to the conventional knowledge known up to the application date, but also further taking into account those not conventionally known currently yet whilst will be transformed into ones deemed as useful for similar purposes.

In addition, the various ranges cited in the specification each comprise the terminals thereof, unless otherwise specified. In addition, when a range, one or more preferable ranges, or a plurality of preferable upper limit values and preferable lower limit values are disclosed for an amount, a concentration or any other value or parameter, they should be deemed as disclosing all ranges formed with arbitrary pairs of any upper limits or preferable values of the ranges with any lower limits or preferable values of the ranges, despite these value pairs being disclosed one by one or not.

In the context of the specification, unless otherwise defined specifically or the meaning provided exceeds the conventional understandings by those skilled, then any hydrocarbon or any group derived from a hydrocarbon having 3 or more carbon atoms (for example propyl, propoxy, butyl, butane, butylene, butenyl, hexane and the like) should be understood to mean same with or without modification by a prefix of "n-". For example, the term propyl is generally understood to represent n-propyl, while butyl is generally understood to represent n-butyl.

In the context of the specification, unless otherwise defined specifically, conversion, yield and selectivity denote respectively a single-pass conversion, a single-pass yield and a single-pass selectivity.

In the context of the specification, phrase "optionally substituted" denotes being optionally substituted by one or more (e.g., 1-3, 1-2 or 1) substituents selected from the group consisting of $C_{1-6}$ linear or branched alkyl optionally substituted by one or more carboxyl or hydroxyl, $C_{2-6}$ linear or branched alkenyl optionally substituted by one or more carboxyl or hydroxyl, $C_{2-6}$ linear or branched alkynyl optionally substituted by one or more carboxyl or hydroxyl, $C_{3-10}$ cycloalkyl optionally substituted by one or more carboxyl or hydroxyl, $C_{6-10}$ aryl optionally substituted by one or more carboxyl or hydroxyl, carboxyl and hydroxyl.

In the context of the specification, term "halogen" denotes fluorine, chlorine, bromine and iodine, preferably chlorine and bromine.

In the context of the specification, without specific indication, all of the percentages, parts, ratios and the like are calculated by weight, unless the calculation by weight does not conform to the conventional understanding by those skilled in the art.

One embodiment according to the present invention provides a process for producing aromatics, wherein the process for producing aromatics comprises following steps a1) and b1):

a1) a step of contacting a compound having a lactone group with a decarboxylation and dimerisation catalyst, under conditions for decarboxylation and dimerisation, to produce a C8 olefin; and b1) a step of contacting the C8 olefin with an aromatization catalyst, under aromatization reaction conditions, to produce aromatics.

According to one embodiment of the present invention, in order to carry out step a1), the compound having a lactone group is contacted with the decarboxylation and dimerisation catalyst, under conditions for the decarboxylation and dimerisation reaction, to produce a C8 olefin. For reducing carbon deposition, increasing the yield of the final aromatics and the like purposes, the catalyst bed contains preferably at least two layers of the decarboxylation and dimerisation catalyst, wherein the decarboxylation and dimerisation catalysts of any two adjacent layers are different. As required, the weight ratio between any two adjacent layers of the decarboxylation and dimerisation catalysts can be such as 10/1 to 1/10. For example, the catalyst bed layers at least comprise, for example, a decarboxylation and dimerisation catalyst A loaded at an upper layer (which contacts with the compound having a lactone group earlier) and a decarboxylation and dimerisation catalyst B loaded at a lower layer (which contacts with the compound having a lactone group later), wherein the decarboxylation and dimerisation catalyst A and the decarboxylation and dimerisation catalyst B are different, at a weight ratio of 10/1 to 1/10.

According to the embodiment of the present invention, the compound having a lactone group contacts respectively with each layer of the decarboxylation and dimerisation catalysts successively. For reducing carbon deposition, increasing the yield of the final aromatics and the like purposes, preferably, regarding any two adjacent layers of the decarboxylation and dimerisation catalysts, the decarboxylation and dimerisation catalyst firstly contacting with the compound having a lactone group (called as a first decarboxylation and dimerisation catalyst hereinafter) is different from the decarboxylation and dimerisation catalyst subsequently contacting with the compound having a lactone group (called as a second decarboxylation and dimerisation catalyst hereinafter), and the both at least have different aciditys. More preferably, the first decarboxylation and dimerisation catalyst has an acidity greater than that of the second decarboxylation and dimerisation catalyst. For example, the acidity of the first decarboxylation and dimerisation catalyst is, possibly 5%, 10%, 30%, 50% or more, higher than that of the second decarboxylation and dimerisation catalyst. Here, the acidity can be expressed, for example, by a Hammett function, $H_0$, and can be measured according to any conventional method known in the art or obtained from technical manuals of prior art, which will not be introduced in more detail here.

Another embodiment according to the present invention provides a process for producing aromatics, wherein the process for producing aromatics comprises following steps a2), b2) and c2):

a2) a step of contacting a compound having a lactone group with a decarboxylation catalyst, under decarboxylation reaction conditions, to produce a C4 olefin;

b2) a step of contacting the C4 olefin with a dimerisation catalyst, under dimerization reaction conditions, to produce a C8 olefin; and c2) a step of contacting the C8 olefin with an aromatization catalyst, under aromatization reaction conditions, to produce aromatics.

According to one embodiment of the present invention, the compound having a lactone group has the structural formula (I):

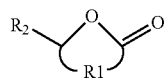

(I)

in formula (I), $R_1$ is selected from the group consisting of optionally substituted $C_{1-20}$ linear or branched alkylene, optionally substituted $C_{2-20}$ linear or branched alkenylene, optionally substituted $C_{2-20}$ linear or branched alkynylene, optionally substituted $C_{3-20}$ cycloalkylene and optionally substituted $C_{6-20}$ arylidene; $R_2$ is selected from the group consisting of hydrogen, optionally substituted $C_{1-20}$ linear or branched alkyl and carboxyl.

According to one embodiment of the present invention, in the formula (I), $R_1$ is selected from the group consisting of optionally substituted $C_{2-10}$ linear or branched alkylene and optionally substituted $C_{2-10}$ linear or branched alkenylene, preferably $C_{2-5}$ linear or branched alkylene, further preferably 1,2-ethylidene.

According to one embodiment of the present invention, in the formula (I), $R_2$ is selected from the group consisting of hydrogen and optionally substituted $C_{1-10}$ linear or branched alkyl, preferably selected from the group consisting of hydrogen and $C_{1-4}$ linear or branched alkyl.

According to one embodiment of the present invention, γ-valerolactone can be particularly provided as an example of the compound having a lactone group.

In the process for producing aromatics according to the present invention, C4 olefin generally denotes a mixture of a plurality of olefins having 4 carbon atoms (an intermediate product), generally comprising 1-butylene, 2-butylene or 2-methylpropene and the like, while C8 olefin generally denotes a plurality of olefins having 8 carbon atoms (an intermediate product), generally comprising 2,4,4-trimethylpentene, 2,5-dimethylhexadiene, 3,4-dimethyl-2-hexylene, 3-methyl-2-heptyl ene, 5-methyl-3-heptylene, 3-methyl-3-heptylene or octylene and the like, but the present invention does not tend to restrict the compositions of these intermediate products.

According to one embodiment of the present invention, the decarboxylation and dimerisation reaction conditions for step a1) comprise: a reaction temperature of 160 to 400 degree Celsius, a reaction pressure of 0.1 to 8 MPa (gage pressure), and a WHSV of the compound having a lactone group of 0.1 to 15 hour$^{-1}$.

According to another embodiment of the present invention, the decarboxylation and dimerisation reaction conditions for step a1) comprise: a reaction temperature of 160 to 300 degree Celsius, a reaction pressure of 0.1 to 4 MPa (gage pressure), and a WHSV of the compound having a lactone group of 0.6 to 5 hour$^{-1}$.

According to one embodiment of the present invention, the decarboxylation reaction conditions for step a2) comprise: a reaction temperature of 100 to 350 degree Celsius, a reaction pressure of 0.1 to 8 MPa (gage pressure), and a WHSV of the compound having a lactone group of 0.1 to 15 hour$^{-1}$.

According to another embodiment of the present invention, the decarboxylation reaction conditions for step a2) comprise: a reaction temperature of 120 to 250 degree Celsius, a preferable reaction pressure of 0.1 to 4 MPa (gage pressure), and a WHSV of the compound having a lactone group of 0.6 to 5 hour'.

According to one embodiment of the present invention, the dimerisation reaction conditions for step b2) comprise: a reaction temperature of 160 to 400 degree Celsius, a reaction pressure of 0.1 to 8 MPa (gage pressure), and a WHSV of the C4 olefin of 0.1 to 15 hour$^{-1}$.

According to another embodiment of the present invention, the dimerisation reaction conditions for step b2) comprise: a reaction temperature of 160 to 300 degree Celsius, a reaction pressure of 0.1 to 4 MPa (gage pressure), and a WHSV of the C4 olefin of 0.6 to 5 hour$^{-1}$.

According to one embodiment of the present invention, the aromatization reaction conditions for step b1) or step c2) comprise: a reaction temperature of 420 to 800 degree Celsius, a reaction pressure of 0.1 to 8 MPa (gage pressure), and a WHSV of the C8 olefin of 0.3 to 10 hour$^{-1}$.

According to another embodiment of the present invention, the aromatization reaction conditions for step b1) or step c2) comprise: a reaction temperature of 450 to 550 degree Celsius, a reaction pressure of 0.1 to 4 MPa (gage pressure), and a WHSV of the C8 olefin of 0.3 to 5 hour$^{-1}$.

According to one embodiment of the present invention, the compound having a lactone group is derived from a biomass material. As the biomass material, those conventionally used to produce aromatics in the art can be provided as examples, specifically, e.g., xylitol, glucose, cellobiose, cellulose, hemicellulose and lignin, etc. These biomass materials can be used alone, or can be used as a combination of two or more thereof.

According to another embodiment of the present invention, paper manufacture sludge, waste paper, bagasse, glucose, wood, corn cob, corn stover and straw stover, and the like, can be specifically provided as further examples of the biomass material. These biomass materials can be used alone, or can be used as a combination of two or more thereof. Here, in the biomass material, the content of cellulose is generally 30-99%, the content of hemicellulose is generally 0-50%, and the content of lignin is generally 1-40%, by weight percent.

According to one embodiment of the present invention, the method for deriving the compound having a lactone group using a biomass material as raw material is not restricted specifically, while those conventionally known in the art can be used. For example, the method for derivation can comprise, for instance, a step of catalytically converting the biomass material (e.g., hydrolysis deoxidation) to produce directly the compound having a lactone group (in particular γ-valerolactone) (e.g., see, Direct conversion of cellulose to levulinic acid and γ-valerolactone using solid acid catalysts, Catal. Sci. Technol., 2013,3, 927-931; Production of levulinic acid and γ-valerolactone (GVL) from cellulose using GVL as a solvent in biphasic systems, Energy Environ. Sci., 2012,5, 8199-8203). Or alternatively, the method for derivation can comprise a step of catalytically converting the biomass material, followed by catalytic hydrogenation, so as to produce the compound having a lactone group. More specifically, the biomass material is firstly catalytically converted through acidolysis, supercritical hydrolysis, catalytic partial oxidation or metal chloride catalysis, to produce levulinic acid (e.g., see, Effective Production of Levulinic Acid from Biomass through Pretreatment Using Phosphoric Acid, Hydrochloric Acid, or Ionic Liquid, Ind. Eng. Chem. Res., 2014, 53 (29), pp 11611-11621), then the levulinic acid produced is contacted with a hydrogenation catalyst under hydrogenation conditions, to produce the compound having a lactone group, in particular γ-valerolactone. As the hydrogenation catalyst, a catalyst comprising 0.1-80% of at least one reactive metal selected from the group consisting of Ni, Ru, Zn, Cu and Pd and 20-99.9% of at least one support selected from the group consisting of $Al_2O_3$, $SiO_2$, $ZrO_2$ and active carbon can be provided as an example. As hydrogenation conditions, an example comprise a reaction temperature of 50-500 degree Celsius, a reaction pressure of 0.1-10.0 MPa (gage pressure), and a WHSV of levulinic acid of 0.1-10.0 $hour^{-1}$, in particular a reaction temperature of 100-300 degree Celsius, a reaction pressure of 0.5-3.0 MPa (gage pressure), and a WHSV of levulinic acid of 0.5-3.0 $hour^{-1}$.

According to one embodiment of the present invention, examples of the decarboxylation and dimerisation catalyst comprise acidic oxide, oxide of bismuth, strongly acidic cation exchange resin, molecular sieve, solid superacid and composite metal oxide and the like. These decarboxylation and dimerisation catalysts can be used alone, or can be used as a combination of two or more thereof.

According to one embodiment of the present invention, examples of the decarboxylation catalyst comprise acidic oxide, strongly acidic cation exchange resin, molecular sieve, solid superacid and composite metal oxide and the like. These decarboxylation catalysts can be used alone, or can be used as a combination of two or more thereof.

According to one embodiment of the present invention, for one or more better technical effects to be achieved by the present invention, examples of the decarboxylation catalyst are preferably acidic oxide, strongly acidic cation exchange resin, solid superacid or a combination thereof, more preferably strongly acidic cation exchange resin, solid superacid or a combination thereof.

According to one embodiment of the present invention, examples of the dimerisation catalyst comprise acidic oxide, oxide of bismuth, strongly acidic cation exchange resin, molecular sieve, solid superacid and composite metal oxide and the like. These dimerisation catalysts can be used alone, or can be used as a combination of two or more thereof.

According to one embodiment of the present invention, for one or more better technical effects to be achieved by the present invention, an example of the dimerisation catalyst is preferably molecular sieve, more preferably ZSM-type molecular sieve.

According to one embodiment of the present invention, examples of the aromatization catalyst comprise molecular sieve, solid superacid and composite metal oxide and the like. These aromatization catalysts can be used alone, or can be used as a combination of two or more thereof.

According to one embodiment of the present invention, for one or more better technical effects to be achieved by the present invention, an example of the dimerisation catalyst is preferably molecular sieve, more preferably ZSM-type molecular sieve.

According to one preferable embodiment of the present invention, for one or more better technical effects to be achieved by the present invention, the acidity D1 of the decarboxylation and dimerisation catalyst and the acidity D2 of the aromatization catalyst satisfy the following formula (I).

$$D1 > D2 \tag{I}$$

According to the preferable embodiment of the present invention, taking a ZSM-type molecular sieve, e.g., ZSM-5, as an example, when being used as decarboxylation and dimerisation catalyst, the molar ratio of Si to Al, calculated as $SiO_2/Al_2O_3$, is generally 80.01 to 250, while being used as aromatization catalyst, the molar ratio of Si to Al, calculated as $SiO_2/Al_2O_3$, is generally 10 to 80.

According to one preferable embodiment of the present invention, for one or more better technical effects to be achieved by the present invention, the acidity D11 of the decarboxylation catalyst, the acidity D12 of the dimerisation catalyst and the acidity D2 of the aromatization catalyst satisfy the following formula (II).

$$D11 > D2 > D12 \tag{II}$$

According to the preferable embodiment of the present invention, taking a ZSM-type molecular sieve, e.g., ZSM-5, as an example, when being used as decarboxylation catalyst, the molar ratio of Si to Al, calculated as $SiO_2/Al_2O_3$, is generally 80 to 500, while being used as dimerisation catalyst, the molar ratio of Si to Al, calculated as $SiO_2/Al_2O_3$, is generally 50 to 150, and when being used as aromatization catalyst, the molar ratio of Si to Al, calculated as $SiO_2/Al_2O_3$, is generally 10 to 50.

According to these preferable embodiments of the present invention, the acidity can be expressed, for example, by a Hammett function, $H_0$, and regarding molecular sieve, can be characterized by $NH_3$-TPD means, which will not be introduced in more detail here.

According to one embodiment of the present invention, examples of the acidic oxide comprise solid oxide of an element from Group IIIA and solid oxide of an element from Group IVA of the periodic table of elements, more specifically, for example, $SiO_2$, $Al_2O_3$ or a combination thereof, in particular $Al_2O_3$—$SiO_2$. These acidic oxides can be used alone, or can be used as a combination of two or more thereof. These acidic oxides can be used directly as a commercially available product or can be produced according to a method known from prior art.

According to one embodiment of the present invention, examples of the oxide of bismuth can comprise various oxides of bismuth, in particular $Bi_2O_3$. The oxide of bismuth can be used directly as a commercially available product or can be produced according to a method known from prior art.

According to one embodiment of the present invention, examples of the strongly acidic cation exchange resin can comprise sulfonic acidic cation exchange resin. Examples of the sulfonic acidic cation exchange resin can comprise macroporous sulfonic acidic cation exchange resin (macroporous sulfonic acidic polystyrene-divinylbenzene resin) and halogen modified sulfonic acidic cation exchange resin. These strongly acidic cation exchange resins can be easily available commercially, or can be prepared according to a method recorded in any of classic documents. The process for producing macroporous sulfonic acidic polystyrene-divinylbenzene resin generally involves adding in droplets a mixture of styrene and divinylbenzene, with a high speed stirring, into an aqueous system comprising dispersant, initiator and porogen for suspension copolymerization, separating polymer spheres (white spheres) obtained from the system, extracting the porogen with a solvent, and further carrying out a sulfonation reaction using dichloroethane as solvent and concentrated sulfuric acid as sulphonating agent, followed finally by filtration, washing and other procedures, to provide the product. In addition, incorporation of halogen atoms, such as fluorine, chlorine, bromine and the like, preferably fluorine, into skeleton of the strongly acidic cation exchange resin, can further increase the temperature tolerance and acidity of the resin. Such a halogen modified sulfonic acidic cation exchange resin can at least be obtained through two ways. One way is to incorporate halogen atoms, e.g. fluorine atoms, into the benzene ring of a sulfonated styrene resin skeleton, whereby not only stabilizing the benzene ring, but also increasing the acidity of the sulfonic group on the benzene ring due to the strong electron-withdrawing function of the halogen. Such resins can be commercially available easily, e.g., Amberlyst® series resins from ROHM & HASS company, D008 resin provided by Hebei Jizhong chemical industry, and the like. Another way is to substitute all hydrogens in the resin skeleton with fluorines (perfluorinated), whereby rendering super strong acidity and superhigh thermostability due to the strong electron-withdrawing property of fluorine. A typical example of such high temperature resistant strongly acidic resins is the Nafion® series resins provided by DuPont company. These strongly acidic cation exchange resins can be used alone, or can be used as a combination of two or more thereof.

According to one embodiment of the present invention, examples of the ZSM-type molecular sieve can comprise ZSM-type molecular sieve, Y-type molecular sieve, beta-type molecular sieve, L-type molecular sieve and MCM-type molecular sieve, in particular ZSM-5, Y-type molecular sieve, beta-type molecular sieve and MCM-41, more particularly ZSM-5. These molecular sieves can be used alone, or can be used as a combination of two or more thereof. These molecular sieves can be used directly as a commercially available product or can be produced according to a method known from prior art.

According to one embodiment of the present invention, examples of the molecular sieve can comprise specifically ZSM-5, ZSM-11, ZSM-22, ZSM-23 and ZSM-38, in particular ZSM-5 (or HZSM-5). Here, the ZSM-type molecular sieve has a molar ratio of Si to Al, calculated as $SiO_2/Al_2O_3$, of generally 10 to 500, preferably 15 to 200. Different categories (comprising those having different molar ratios of Si to Al) of ZSM-type molecular sieves can be used alone, or can be used as a combination of two or more thereof.

According to one embodiment of the present invention, the Y-type molecular sieve has a molar ratio of Si to Al, calculated as $SiO_2/Al_2O_3$, of generally 2 to 70, preferably 3 to 50. Different categories (comprising those having different molar ratios of Si to Al) of Y-type molecular sieves can be used alone, or can be used as a combination of two or more thereof.

According to one embodiment of the present invention, the beta-type molecular sieve has a molar ratio of Si to Al, calculated as $SiO_2/Al_2O_3$, of generally 10 to 150, preferably 15 to 65. Different categories (comprising those having different molar ratios of Si to Al) of beta-type molecular sieves can be used alone, or can be used as a combination of two or more thereof.

According to one embodiment of the present invention, the L-type molecular sieve has a molar ratio of Si to Al, calculated as $SiO_2/Al_2O_3$, of generally 5 to 100, preferably 6 to 35.

Different categories (comprising those having different molar ratios of Si to Al) of L-type molecular sieves can be used alone, or can be used as a combination of two or more thereof.

According to one embodiment of the present invention, examples of the MCM-type molecular sieve can comprise specifically MCM-22 and MCM-41. Here, the MCM-type molecular sieve has a molar ratio of Si to Al, calculated as $SiO_2/Al_2O_3$, of generally 20 to 250, preferably 40 to 150. Different categories (comprising those having different molar ratios of Si to Al) of MCM-type molecular sieves can be used alone, or can be used as a combination of two or more thereof.

According to one embodiment of the present invention, the molecular sieve is used in the form of a molecular sieve composition A, comprising: a1) 20 to 80 parts by weight of the molecular sieve, b1) 20 to 80 parts by weight of a binder, and c1) 0 to 10 parts by weight of an auxiliary. In particular, the molecular sieve composition A comprises: a1) 50 to 80 parts by weight of the molecular sieve, b1) 20 to 50 parts by weight of a binder, and c1) 0.01 to 10 parts by weight (or 0.01 to 5 parts by weight) of an auxiliary.

According to another embodiment of the present invention, the molecular sieve is used in the form of a molecular sieve composition B, comprising: a2) 90 to 99.99 parts by weight of the molecular sieve, and c2) 0.01 to 10 parts by weight of an auxiliary. In particular, the molecular sieve composition B comprises: a2) 95 to 99.99 parts by weight of the molecular sieve, and c2) 0.01 to 5 parts by weight of an auxiliary.

According to one embodiment of the present invention, these molecular sieve compositions can be used directly as a commercially available product or can be produced according to a method known from prior art. Specifically, as a method of producing the molecular sieve composition, the following method can be mentioned, for example: mixing and kneading molecular sieve, binder and, if needed, extrusion aid, pore-expanding agent and water to provide a mixture, extruding and shaping, followed by drying at a temperature of 100-200 degree Celsius for 1-24 h, and calcining at a temperature of 400-700 degree Celsius for 1-10 h. Examples of the extrusion aid can comprise those conventionally used in the art, such as sesbania powder, polyethylene glycol or sodium carboxymethylcellulose and the like; while examples of the pore-expanding agent can comprise those conventionally used in the art, such as citric acid, oxalic acid or ethylenediamine tetraacetic acid and the like. In general, the extrusion aid and pore-expanding agent are added in a total amount not greater than 10 wt % of the total weight of the mixture. As required, acid can also be added during shaping. Examples of the acid can comprise inorganic acid, acetic acid or an aqueous solution thereof and the like, in particular an aqueous solution of nitric acid, sulfuric acid or phosphoric acid. In general, the aqueous solution of acid is added in an amount of 50-90 wt % of the total weight of the mixture.

According to one embodiment of the present invention, the auxiliary can be incorporated during the production of the molecular sieve composition or after the production of the molecular sieve composition; or alternatively can be incorporated firstly into the molecular sieve followed by producing the molecular sieve composition using the thus obtained molecular sieve, without specific restriction thereto. Examples of a method of incorporating the auxiliary can comprise those methods conventionally used in the art, in particular ion-exchange method or immersion method. In the methods, auxiliary is generally used in the form of a precursor. Accordingly, examples of the precursor of a metal auxiliary can comprise nitrate, sulfate, acetate or chloride salt and the like of the metal; the examples the precursor of boron auxiliary can comprise boric acid or borax; while examples of the precursor of phosphorus auxiliary can comprise diammonium phosphate and so on.

According to one embodiment of the present invention, examples of the binder can comprise those binders conventionally used in the art for producing a molecular sieve composition, more specifically, for example, silica sol, pseudo-boehmite, alumina, acid treated clay, kaolin, montmorillonite and bentonite and the like, in particular alumina (in particular γ-alumina), pseudo-boehmite and montmorillonite and the like. These binders can be used alone, or can be used as a combination of two or more thereof.

According to one embodiment of the present invention, examples of the auxiliary can comprise Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, in particular Ca, K, Mg, Cr, Mo, Fe, Ni, Cu, Zn, Ga, Ru, Pd, Pt, Ag, B, Sn, P, La and Ce and the like. These auxiliaries can be used alone, or can be used as a combination of two or more thereof. The auxiliary is preferably Zn, Ga, Sn or a combination thereof.

According to one embodiment of the present invention, examples of the molecular sieve can comprise particularly M/ZSM-5, wherein M is selected from the group consisting of Zn, Ga, Sn or a combination thereof. The molecular sieve or a molecular sieve composition comprising the molecular sieve is especially useful as the aromatization catalyst. The molecular sieves can be used directly as a commercially available product or can be produced according to a method known from prior art.

According to one embodiment of the present invention, examples of the solid superacid can comprise those conventionally used as solid acid catalyst, more specifically, for example, supported Lewis acid solid superacid, composite inorganic metal salt/Lewis acid superacid and solid as sulfated metal oxide superacid. These solid superacids can be used alone, or can be used as a combination of two or more thereof. These solid superacids can be used directly as a commercially available product or can be produced according to a method known from prior art. According to one embodiment of the present invention, the supported Lewis acid solid superacid comprises a support and a Lewis acid on the support. Examples of the support can comprise solid oxide of an element from Group IIIA and solid oxide of an element from Group IVA of the periodic table, in particular $SiO_2$, $B_2O_3$ and $Al_2O_3$. These supports can be used alone, or can be used as a combination of two or more thereof. Examples of Lewis acid can comprise halide of an element from Group VB, halide of an element from Group IIIA and halide of an element from Group VA of the periodic table of elements, in particular halide of an element from Group VB and halide of an element from Group VA of the periodic table of elements, more particularly $PF_3$, $AsF_3$, $SbF_3$, $BiF_3$, $SbF_5$, $TaF_3$, $VF_3$ and $NbF_3$. Here, fluoride is preferably used as a halide. These Lewis acids can be used alone, or can be used as a combination of two or more thereof. More specifically, examples of the supported Lewis acid solid superacid can comprise $SbF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$ and $NbF_3/Al_2O_3$—$B_2O_3$. These supported Lewis acid solid superacids can be used alone, or can be used as a combination of two or more thereof.

According to one embodiment of the present invention, in the supported Lewis acid solid superacid, the Lewis acid is supported in an amount of 1 to 30 wt %, preferably 1 to 15 wt %, relative to the weight of the support.

According to one embodiment of the present invention, the solid inorganic metal salt/Lewis acid composite superacid is a composite consisting of an inorganic metal salt and a Lewis acid. Examples of the inorganic metal salt can comprise inorganic acid salt of a metal element from Group IB, inorganic acid salt of a metal element from Group IIB, inorganic acid salt of a metal element from Group VII and inorganic acid salt of a metal element from Group VIII of the periodic table of elements. Here, examples of the inorganic acid salt can particularly comprise haloid acid salt, especially hydrochloride. These inorganic metal salts can be used alone, or can be used as a combination of two or more thereof. Examples of the Lewis acid can comprise halide of an element from Group VB, halide of an element from Group IIIA and halide of an element from Group VA of the periodic table of elements, in particular halide of an element from Group IIIA of the periodic table of elements. Here, chloride is preferably used as a halide. These Lewis acids can be used alone, or can be used as a combination of two or more thereof. The solid inorganic metal salt/Lewis acid composite superacid is preferably $AlCl_3$-$CuCl_2$. These solid superacids as inorganic metal salt/Lewis acid composite can be used alone, or can be used as a combination of two or more thereof.

According to one embodiment of the present invention, in the solid inorganic metal salt/Lewis acid composite superacid, the weight ratio between the inorganic metal salt and the Lewis acid is 1-30:100. preferably 1-15:100.

According to one embodiment of the present invention, in the solid sulfated metal oxide superacid, examples of the metal oxide can comprise oxide of a metal element from Group IVB of the periodic table of elements (called as oxide A hereinafter), or oxide obtained by modifying the oxide A with a modifying element comprising a metal element from Group IIIA, a metal element from Group VIIB, a noble metal element from Group VIII, a base metal element from Group VIII, a metal element from Group VIB or lanthanide metal element of the periodic table of elements (called as oxide B hereinafter). These metal oxides can be used alone, or can be used as a combination of two or more thereof. These modifying elements can be used alone, or can be used as a combination of two or more thereof. Examples of the oxide A can comprise $ZrO_2$, $TiO_2$ or a combination thereof. Examples of the modifying element can comprise Fe, Pt, Re, Al, W, Cr, Mo, Mn or a combination thereof. In the oxide B, the metal element from Group IIIA of the periodic table of elements is generally present in the form of an oxide, the metal element from Group VIIB is generally present in the form of an oxide, the noble metal element from Group VIII is generally present in the form of a metal elementary substance, the base metal element from Group VIII is generally present in the form of an oxide, the metal element from Group VIB is generally present in the form of an oxide, and the lanthanide metal element is generally present in the form of an oxide. Examples of the solid sulfated metal oxide superacid can particularly comprise $SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$, $SO_4^{2-}/ZrO_2$—$Fe_2O_3$—$MnO_2$, W modified $SO_4^{2-}/Al_2O_3$—$ZrO_2$, and Mo modified $SO_4^{2-}/Al_2O_3$—$ZrO_2$. The aforementioned solid superacids as sulfated metal oxide can be used alone, or can be used as a combination of two or more thereof.

According to one embodiment of the present invention, in the oxide B, the weight ratio of the modifying element in the form of oxide (calculated as oxide) to the oxide A is generally 0.1-25:100, preferably 0.5-10:100, and the weight ratio of the modifying element in the form of metal elementary substance (calculated as metal) to the oxide A is generally 0.1-15:100, preferably 0.3-6:100.

According to one embodiment of the present invention, in the solid sulfated metal oxide superacid, the metal oxide generally has a sulfated rate of 0.5-25 wt %, preferably 1-8 wt %.

According to one embodiment of the present invention, the method of producing the solid sulfated metal oxide superacid is not restricted specifically, for which those conventionally known in the art can be used, specifically e.g., precipitation-immersion method (for example, see the document "Progress in $SO_4^{2-}/M_xO_y$ solid superacid catalysts, Applied Chemical Industry, 2014, vol43, 1879-1883").

According to one embodiment of the present invention, examples of the composite metal oxide can comprise a composite oxide of a metal element from Group IVB of the periodic table of elements (called as oxide C hereinafter) with another oxide (called as oxide D hereinafter). Examples of the oxide C can comprise $ZrO_2$, $TiO_2$ or a combination thereof, in particular $ZrO_2$. Examples of the oxide D can comprise oxide of a metal element from Group IIIA, oxide of a metal element from Group VII, oxide of a metal element from Group VIB, and oxide of a lanthanide metal element, of the periodic table of elements, and the like, more specifically $B_2O_3$, $Al_2O_3$, $MnO_2$, $Cr_2O_3$, $CrO_3$, $MoO_3$, $WO_3$, $La_2O_3$ and $CeO_2$ and the like, in particular $MnO_2$, $MoO_3$, $WO_3$, $La_2O_3$ and $CeO_2$ and the like. These oxides D can be used alone, or can be used as a combination of two or more thereof. Examples of the composite metal oxide can comprise a composite oxide of $ZrO_2$ with one or more oxides D selected from the group consisting of $MnO_2$, $Mo_2O_3$, $WO_3$, $La_2O_3$ and $CeO_2$.

According to one embodiment of the present invention, in the composite metal oxide, the ratio of the oxide C to the oxide D is generally 60-99.9: 0.1-40, preferably 60-99:1-40, calculated in parts by weight.

According to one embodiment of the present invention, the composite metal oxide can be used directly as a commercially available product or can be produced according to a method known from prior art. Examples of the method of producing the composite metal oxide can comprise immersion method or precipitation method, and the like. More specifically, for example, a useful immersion method comprises immersing tungsten, molybdenum, cerium, lanthanum or manganese as a saline solution onto zirconia, throwing away the spare liquid after 12 to 48 hours of immersion, drying at a temperature of 100 to 200 degree Celsius, evaporating out of water to leave the active components, followed by treatment by calcining and activating procedures to provide the composite metal oxide; or alternatively, a useful precipitation method comprises adding simultaneously an aqueous solution of metal salt of tungsten, molybdenum, cerium, lanthanum or manganese, an aqueous solution of a metal salt of zirconium and an aqueous ammonia as precipitant to generate a solid precipitation, washing, filtrating and drying the precipitation generated, and calcining at a temperature of 400 to 600 degree Celsius to provide the composite metal oxide.

According to one embodiment of the present invention, the step a2), the step b2), the step c2), the step a1) and the step b1) each can be respectively carried out in one or more reactors. Examples of the reactor can comprise bed reactor, in particular fixed bed reactor, fluidized bed reactor, ebullated bed reactor or a combination thereof. At this point, the reactor can be operated in batched, or continuously, without specific restriction.

According to one embodiment of the present invention, one or more of the step a2), the step b2), the step c2), the step a1) and the step b1) each can be respectively carried out in inert gas atmosphere or reducing gas atmosphere. Examples of the inert gas atmosphere can comprise $N_2$, $CO_2$, He, Ar or a combination thereof. Examples of the reducing gas atmosphere can comprise CO, $H_2$ or a combination thereof.

After producing the aromatics (namely, an aromatic product rich in xylene) according to the process for producing aromatics of the present invention, p-xylene can be separated from the aromatic product. Thus, the present invention further relates to a process for producing p-xylene, comprising a step of producing aromatics according to the process for producing aromatics of the present invention; and a step of separating p-xylene from the aromatics.

According to one embodiment of the present invention, the method of separating p-xylene from the aromatics is not specifically restricted, while those conventionally known in the art can be used directly. As compared with the aromatics obtained according a method of prior art, the aromatics obtained according to the present invention is relatively rich in xylene, the separation method has the characters of reduced operation cost and decreased operation complexity. In general, the aromatics can directly provide, after separation, a p-xylene product with a purity of 70-99.9 wt %.

According to one embodiment of the present invention, terephthalic acid can be produced using p-xylene produced according to the present invention introduced above as a raw material. Thus, the present invention further relates to a process for producing terephthalic acid, comprising a step of producing p-xylene according to the aforementioned process for producing p-xylene of the present invention; and a step of converting the p-xylene into terephthalic acid.

According to one embodiment of the present invention, the method of converting p-xylene into terephthalic acid is not specifically restricted, while those conventionally known in the art can be used directly.

According to one embodiment of the present invention, a device for producing aromatics is also provided, which device is so constructed as to be particularly useful for conducting the process for producing aromatics according to the present invention introduced above.

According to one embodiment of the present invention, the device for producing aromatics comprises the units of:

a decarboxylation and dimerisation unit, constructed as being capable of contacting a compound having a lactone group with a decarboxylation and dimerisation catalyst, under conditions for decarboxylation and dimerization reaction, to produce a C8 olefin; and an aromatization unit, constructed as being capable of contacting the C8 olefin with an aromatization catalyst under aromatization reaction conditions, to produce aromatics.

According to one embodiment of the present invention, the device for producing aromatics can optionally further comprise a catalytic conversion unit, or the device for producing aromatics can optionally further comprise a combination of a catalytic conversion unit with a catalytic hydrogenation unit. Here, the catalytic conversion unit is constructed as allowing catalytic conversion of a biomass material to generate a product comprising the compound having a lactone group, while the catalytic hydrogenation unit is constructed as being capable of increasing the proportion of the compound having a lactone group in the product through catalytically hydrogenating the product.

EXAMPLES

The present invention will be further illustrated in more detail referring to the Examples below, whilst the present invention is not restricted to these Examples.

In the context of the specification, the yield of carbon as xylene is calculated according to the formula below.

The yield of carbon as xylene (%)=weight of xylene as a reaction product (g)/carbon weight of the compound having a lactone group as a reaction raw material*100%.

An example for calculation is as follows:

100 g of valerolactone is used as the compound having a lactone group, which comprises 68 g of carbon; then, if 50 g of xylene is obtained after reaction, the yield of carbon as xylene is 73.5%.

Example 1

Decarboxylation and dimerisation catalyst ZSM-5: 35 g of ZSM-5 having a ratio of Si:Al of 38 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Production of aromatization catalyst ZSM-5: 35 g of hydrogenous ZSM-5 having a ratio of Si:Al of 100 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Angelica lactone was added into a decarboxylation and dimerisation reactor R1, in which the upper layer of the catalyst bed layers was loaded with $Al_2O_3$-$SiO_2$ catalyst (produced according to Example 1 of CN1393425A), and the lower layer of the catalyst bed layers was loaded with the decarboxylation and dimerisation catalyst ZSM-5 produced above, two catalyst layers having a same packing height. Decarboxylation and dimerisation was conducted under conditions of a temperature of 300 degree Celsius and a WHSV of 1.5 $h^{-1}$, resulting in a conversion of 87%, and a selectivity to C8 olefin of 79%. After separation, the C8 olefin was fed into an aromatization reactor R2 for aromatization under the actions of a temperature of 450 degree Celsius, the aromatization catalyst ZSM-5, and a space velocity of 2 $h^{-1}$, to provide a stream containing a xylene product, with a selectivity to xylene of 79%, and a yield of carbon as xylene of 54.3%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 2

1000 g of straw stover was weighed and placed into a pressured reactor, 5000 g of water was added, and a 5mol/L of sulphuric acid solution having 7 wt % of water was further added. The temperature was increased to 210 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 382 g. The levulinic acid obtained was hydrogenated on RuSn/C loaded with 2% metal in a fixed bed to provide γ-valerolactone, with a conversion of 99% and a yield of the product of 98%.

Production of decarboxylation and dimerisation catalyst A: a Mo modified $SO_2^{2-}/Al_2O_3$—$ZrO_2$ catalyst (produced according to Example 2 of CN200910011627.6, wherein for the incorporation of reactive metal using the method, only Mo was incorporated without incorporation of Ni).

Production of decarboxylation and dimerisation catalyst ZSM-5-B: 65 g of hydrogenous ZSM-5 having a ratio of Si:Al of 100 was mixed with 35 g of pseudo-boehmite, 3.5 g of sesbania powder was added, and mixed homogeneously. Then, 108 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Production of aromatization catalyst ZSM-5: 80 g of ZSM-5 having a ratio of Si:Al of 150 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which the upper layer of the catalyst bed layers was loaded with the decarboxylation and dimerisation catalyst A, and the lower layer of the catalyst bed layers was loaded with the decarboxylation and dimerisation catalyst ZSM-5-B, two catalyst layers having a same packing height. Decarboxylation and dimerisation was conducted under conditions of a temperature of 280 degree Celsius and a WHSV of 1.5 h$^{-1}$, resulting in a conversion of 93%, and a selectivity to C8 olefin of 86%. After separation, the C8 olefin was fed into an aromatization reactor R2 for aromatization under the actions of a temperature of 450 degree Celsius, the aromatization catalyst ZSM-5, and a space velocity of 2 h$^{-1}$, to provide a stream containing a xylene product, with a selectivity to xylene of 83%, and a yield of carbon as xylene of 66.4%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from bottom. Hydrogen out of the column top could be used as a raw material for hydrogenating oligomers into gasoline or diesel oil, while the heavy component from the column bottom could be used as a raw material for diesel oil or be combusted to supply heat.

Example 3

Production of decarboxylation and dimerisation catalyst A: 50 g of beta having a ratio of Si:Al of 30 was mixed with 50 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Decarboxylation and dimerisation catalyst B: 35 g of ZSM-5 having a ratio of Si:Al of 100 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst HZSM-5: 35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

δ-valerolactone was added into a decarboxylation and dimerisation reactor R1, in which the upper layer of the catalyst bed layers was loaded with the decarboxylation and dimerisation catalyst A, and the lower layer of the catalyst bed layers was loaded with the decarboxylation and dimerisation catalyst B, two catalyst layers having a same packing height. Decarboxylation and dimerisation was conducted under conditions of a temperature of 280 degree Celsius and a WHSV of 1.5 h$^{-1}$, resulting in a conversion of 99%, and a selectivity to C8 olefin of 93%. After separation, the C8 olefin was fed into an aromatization reactor R2 for aromatization under the actions of a temperature of 450 degree Celsius, an aromatization catalyst HZSM-5, and a space velocity of 2 h$^{-1}$, to provide a stream containing a xylene product, with a selectivity to xylene of 86%, and a yield of carbon as xylene of 79.2%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from bottom. Hydrogen out of the column top could be used as a raw material for hydrogenating oligomers into gasoline or diesel oil, while the heavy component from the column bottom could be used as a raw material for diesel oil or be combusted to supply heat.

Example 4

Decarboxylation and dimerisation catalyst B: 35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst La-HY: 35 g of HY-type molecular sieve having a ratio of Si:Al of 6 was mixed with 35 g of auxiliary of γ-alumina, 2.7 g of sodium carboxymethylcellulose was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a further catalyst precursor, followed by loading 3% of La through an immersion method, to provide the La-Y catalyst.

γ-lactone was added into a decarboxylation reactor R1, in which the upper layer of the catalyst bed layers was loaded with $SO_4^{2-}/Al_2O_3$—$ZrO_2$ catalyst (produced according to Example 1 of CN200910011627.6), and the lower layer of the catalyst bed layers was loaded with the decarboxylation and dimerisation catalyst B produced above, two catalyst layers having a same packing height. Decarboxylation and dimerisation was conducted under conditions of a temperature of 250 degree Celsius and a WHSV of 1.5 h$^{-1}$, resulting in a conversion of 99%, and a selectivity to C8 olefin of 89%. After separation, the C8 olefin was fed into an aromatization reactor R2 for aromatization under the actions of a temperature of 450 degree Celsius, an aromatization catalyst La-HY, and a space velocity of 2 to provide a stream containing a xylene product, with a selectivity to xylene of 88%, and a yield of carbon as xylene of 77.5%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from bottom. Hydrogen out of the column top could be used as a raw material for hydrogenating oligomers into gasoline or diesel oil, while the heavy component from the column bottom could be used as a raw material for diesel oil or be combusted to supply heat.

Example 5

Decarboxylation and dimerisation catalyst B: 60 g of Y-type molecular sieve having a ratio of Si:Al of 8 was mixed with 40 g of an auxiliary of γ-alumina, 3.9 g of sesbania powder was added, and mixed homogeneously. Then, 68.6 g of an aqueous solution of phosphoric acid comprising 5.5 wt % of phosphoric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst MCM-22: 70 g of Y having a ratio of Si:Al of 10 was mixed with 30 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-heptalactone was added into a decarboxylation and dimerisation reactor R1, in which the upper layer of the catalyst bed layers was loaded with Amberlyst catalyst (Amberlyst™ 15WET), and the lower layer of the catalyst bed layers was loaded with the decarboxylation and dimerisation catalyst B produced above, two catalyst layers having a same packing height.

Decarboxylation and dimerisation was conducted under conditions of a temperature of 180 degree Celsius and a WHSV of 1.5 $h^{-1}$, resulting in a conversion of 96%, and a selectivity to C8 olefin of 81%. After separation, the C8 olefin was fed into an aromatization reactor R2 for aromatization under the actions of a temperature of 500 degree Celsius, an aromatization catalyst MCM-22, and a space velocity of 2 to provide a stream containing a xylene product, with a selectivity to xylene of 94%, and a yield of carbon as xylene of 73.1%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 6

Decarboxylation and dimerisation catalyst B: 35 g of ZSM-5 having a ratio of Si:Al of 100 was mixed with 45 g of pseudo-boehmite, 3.2 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst ZSM-5: 35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which the upper layer of the catalyst bed layers was loaded with Amberlyst catalyst (Amberlyst™ 15WET), and the lower layer of the catalyst bed layers was loaded with the decarboxylation and dimerisation catalyst B produced above, two catalyst layers having a same packing height. Decarboxylation and dimerisation was conducted under conditions of a temperature of 180 degree Celsius and a WHSV of 1.5 $h^{-1}$, resulting in a conversion of 96%, and a selectivity to C8 olefin of 91%. After separation, the C8 olefin was fed into an aromatization reactor R2 for aromatization under the actions of a temperature of 450 degree Celsius, the aromatization catalyst ZSM-5, and a space velocity of 2 $h^{-1}$, to provide a stream containing a xylene product, with a selectivity to xylene of 86%, and a yield of carbon as xylene of 75.1%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 7

Decarboxylation and dimerisation catalyst: 60 g of Y having a ratio of Si:Al of 10 was mixed with 40 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a further catalyst precursor, followed by loading 3% of La through an immersion method, to provide the La-HY catalyst.

Aromatization catalyst ZSM-5: 35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which decarboxylation and dimerisation was conducted under conditions of the decarboxylation and dimerisation catalyst, a temperature of 180 degree Celsius and a WHSV of 1.5 $h^{-1}$, resulting in a conversion of 91%, and a selectivity to C8 olefin of 89%. After separation, the C8 olefin was fed into an aromatization reactor R2 for aromatization under the actions of a temperature of 550 degree Celsius, an aromatization catalyst ZSM-5, and a space velocity of 1.5 $h^{-1}$, to provide a stream containing a xylene product, with a selectivity to xylene of 86%, and a yield of carbon as xylene of 69.7%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 8

Production of decarboxylation catalyst A: 50 g of beta having a ratio of Si:Al of 20 was mixed with 50 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Production of dimerisation catalyst B: 65 g of hydrogenous ZSM-5 having a ratio of Si:Al of 100 was mixed with 35 g of pseudo-boehmite, 3.5 g of sesbania powder was added, and mixed homogeneously. Then, 108 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Production of aromatization catalyst ZSM-5: 80 g of ZSM-5 having a ratio of Si:Al of 150 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which the upper layer of the catalyst bed layers was loaded with decarboxylation catalyst A, and the lower layer of the catalyst bed layers was loaded with the decarboxylation and dimerisation catalyst B, two catalyst layers having a same packing height. Decarboxylation and dimerisation was conducted under conditions of a temperature of 280 degree Celsius and a WHSV of 1.5 h$^{-1}$, resulting in a conversion of 96%, and a selectivity to C8 olefin of 93%. After separation, the C8 olefin was fed into an aromatization reactor R2 for aromatization under the actions of a temperature of 500 degree Celsius, an aromatization catalyst ZSM-5, and a space velocity of 1.5 h$^{-1}$, to provide a stream containing a xylene product, with a selectivity to xylene of 88%, and a yield of carbon as xylene of 78.6%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 9

Production of decarboxylation catalyst A: 50 g of beta having a ratio of Si:Al of 20 was mixed with 50 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst. Production of dimerisation catalyst B: 65 g of hydrogenous ZSM-5 having a ratio of Si:Al of 100 was mixed with 35 g of pseudo-boehmite, 3.5 g of sesbania powder was added, and mixed homogeneously. Then, 108 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Production of aromatization catalyst ZSM-5: 80 g of ZSM-5 having a ratio of Si:Al of 150 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which the upper layer of the catalyst bed layers was loaded with the decarboxylation catalyst A, and the lower layer of the catalyst bed layers was loaded with the decarboxylation and dimerisation catalyst B, two catalyst layers having a same packing height. Decarboxylation and dimerisation was conducted under conditions of a temperature of 280 degree Celsius and a WHSV of 1.5 h$^{-1}$, resulting in a conversion of 97%, and a selectivity to C8 olefin of 92%.

After separation, the C8 olefin was fed into an aromatization reactor R2 for aromatization under the actions of a temperature of 450 degree Celsius, an aromatization catalyst ZSM-5, and a space velocity of 1.5 h$^{-1}$, to provide a stream containing a xylene product, with a selectivity to xylene of 90%, and a yield of carbon as xylene of 80.3%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 10

Decarboxylation and dimerisation catalyst A: 60 g of Y having a ratio of Si:Al of 6 was mixed with 40 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Decarboxylation and dimerisation catalyst B: 35 g of ZSM-5 having a ratio of Si:Al of 50 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst Zn-ZSM-5: 35 g of ZSM-5 molecular sieve having a ratio of Si:Al of 150 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a pre-catalyst.

The pre-catalyst was immersed with Zn, in an amount of 1.5 wt % of the pre-catalyst, and dried and calcined to provide the Zn-ZSM-5.

γ-valerolactone was added into a decarboxylation and dimerisation reactor R1, in which the upper layer of the catalyst bed layers was loaded with the decarboxylation and dimerisation catalyst A produced above, and the lower layer of the catalyst bed layers was loaded with the decarboxylation and dimerisation catalyst B produced above, two catalyst layers having a same packing height. Decarboxylation and dimerisation was conducted under conditions of a temperature of 250 degree Celsius and a WHSV of 1.5 $h^{-1}$, resulting in a conversion of 99%, and a selectivity to C8 olefin of 96%. After separation, the C8 olefin was fed into an aromatization reactor R2 for aromatization under the actions of a temperature of 480 degree Celsius, an aromatization catalyst Zn-ZSM-5, and a space velocity of 1.5 $h^{-1}$, to provide a stream containing a xylene product, with a selectivity to xylene of 91%, and a yield of carbon as xylene of 86.5%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom. Hydrogen out of the column top could be used as a raw material for hydrogenating oligomers into gasoline or diesel oil, while the heavy component from the column bottom could be used as a raw material for diesel oil or be combusted to supply heat.

Example 11

Decarboxylation and dimerisation catalyst A: 60 g of Y having a ratio of Si:Al of 6 was mixed with 40 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Decarboxylation and dimerisation catalyst B: 35 g of ZSM-5 having a ratio of Si:Al of 50 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst Ga-ZSM-5: 35 g of ZSM-5 molecular sieve having a ratio of Si:Al of 150 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a pre-catalyst. The pre-catalyst was immersed with Ga, in an amount of 1.5 wt % of the pre-catalyst, and dried and calcined to provide the Ga-ZSM-5.

γ-valerolactone was added into a decarboxylation and dimerisation reactor R1, in which the upper layer of the catalyst bed layers was loaded with the decarboxylation and dimerisation catalyst A produced above, and the lower layer of the catalyst bed layers was loaded with the decarboxylation and dimerisation catalyst B produced above, two catalyst layers having a same packing height. Decarboxylation and dimerisation was conducted under conditions of a temperature of 250 degree Celsius and a WHSV of 1.5 $h^{-1}$, resulting in a conversion of 99%, and a selectivity to C8 olefin of 95%. After separation, the C8 olefin was fed into an aromatization reactor R2 for aromatization under the actions of a temperature of 450 degree Celsius, an aromatization catalyst Ga-ZSM-5, and a space velocity of 1.5 $h^{-1}$, to provide a stream containing a xylene product, with a selectivity to xylene of 91%, and a yield of carbon as xylene of 85.6%. The olefin not reacted completely could be recycled to the dimer reactor for continued reaction. The olefin obtained was further separated to provide light aromatics comprising benzene, toluene and the like, simultaneously providing PX in high-purity. In addition, an additional part was obtained as a heavy component from the column bottom.

Hydrogen out of the column top could be used as a raw material for hydrogenating oligomers into gasoline or diesel oil, while the heavy component from the column bottom could be used as a raw material for diesel oil or be combusted to supply heat.

Comparative Example 1

Decarboxylation and dimerisation catalyst A: 35 g of ZSM-5 having a ratio of Si:Al of 150 was mixed with 35 g of pseudo-Boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Decarboxylation and dimerisation catalyst B: 35 g of ZSM-5 having a ratio of Si:Al of 25 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

Aromatization catalyst ZSM-5: 35 g of ZSM-5 molecular sieve having a ratio of Si:Al of 500 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide the catalyst.

γ-valerolactone was added into a decarboxylation and dimerisation reactor R1, in which the upper layer of the catalyst bed layers was loaded with the decarboxylation and dimerisation catalyst A, and the lower layer of the catalyst bed layers was loaded with the decarboxylation and dimerisation catalyst B produced above, two catalyst layers having a same packing height. Decarboxylation and dimerisation was carried out under conditions of a temperature of 250 degrees C. and a WHSV of 1.5 $h^{-1}$, resulting in a conversion of 83%, and a dramatically decreased selectivity to C8 olefin of 26% due to too strong acidity of the decarboxylation and dimerisation catalyst B which led the intermediate products including C4 olefin and the like to rapid coking. The C8 olefin was fed, after separation, into an aromatization reactor R2 for aromatization under the actions of a temperature of 450 degree Celsius, an aromatization catalyst ZSM-5, and a space velocity of 1.5 $h^{-1}$, to provide a stream containing a xylene product, with a selectivity to xylene of 56%. The olefin not reacted completely could be recycled to the dimer reactor for continued reaction. However, owing to the catalyst deactivation, catalyst performance degraded so rapidly that PX in high-purity could not be obtained.

Although the embodiments of the present invention have been illustrated in detail above referring to the Examples, it should be understood that the protection scopes of the present invention are no restricted thereto; instead, the protection scopes are defined by the claims attached. Those skilled in the art can make appropriate modification to these embodiments without departing the technical idea and spirit of the invention, while the modified embodiments are also included within the protection scopes of the invention obviously.

The invention claimed is:

1. A process for producing aromatics, comprising the steps of a1) and b1) or comprising the steps of a2), b2) and c2):

a1) a step of contacting a compound having a lactone group with a decarboxylation and dimerisation catalyst, under conditions for decarboxylation and dimerisation reaction, to produce a C8 olefin; and b1) a step of contacting the C8 olefin with an aromatization catalyst under aromatization reaction conditions, to produce aromatics, wherein the acidity of the decarboxylation and dimerisation catalyst is higher than the acidity of the aromatization catalyst, or a2) a step of contacting a compound having a lactone group with a decarboxylation catalyst, under decarboxylation reaction conditions, to produce a C4 olefin; and b2) a step of contacting the C4 olefin with a dimerisation catalyst, under dimerization reaction conditions, to produce a C8 olefin; and c2) a step of contacting the C8 olefin with an aromatization catalyst under aromatization reaction conditions, to produce aromatics, wherein the acidity of the decarboxylation catalyst is higher than the acidity of the aromatization catalyst, and the acidity of the aromatization catalyst is higher than the acidity of the dimerisation catalyst, wherein, the compound having a lactone group has the structural formula (I):

in formula (I), $R_1$ is selected from the group consisting of optionally substituted $C_{1-20}$ linear or branched alkylene, optionally substituted $C_{2-20}$ linear or branched alkenylene, optionally substituted $C_{2-20}$ linear or branched alkynylene, optionally substituted $C_{3-20}$ cycloalkylene and optionally substituted $C_{6-20}$ arylidene, and $R_2$ is selected from the group consisting of hydrogen, optionally substituted $C_{1-20}$ linear or branched alkyl and carboxyl, wherein the compound of formula (I) is obtained from catalytic conversion of a compound selected from the group consisting of xylitol, glucose, cellobiose, cellulose, hemicellulose, and lignin, wherein the decarboxylation and dimerisation catalyst is one or more selected from the group consisting of acidic oxide, oxide of bismuth, strongly acidic cation exchange resin, molecular sieve, solid superacid, and composite metal oxide;

the decarboxylation catalyst is one or more selected from the group consisting of acidic oxide, strongly acidic cation exchange resin, molecular sieve, solid superacid, and composite metal oxide;

the dimerisation catalyst is one or more selected from the group consisting of acidic oxide, oxide of bismuth, strongly acidic cation exchange resin, molecular sieve, solid superacid and composite metal oxide; and the aromatization catalyst is one or more selected from the group consisting of molecular sieve, solid superacid, and composite metal oxide.

2. The process according to claim 1, wherein step a1) is carried out at a reaction temperature of 160 to 400 degree Celsius under a reaction pressure of 0.1 to 8 MPa and at a WHSV for the compound having a lactone group of 0.1 to 15 $hour^{-1}$; step a2) is carried out at a reaction temperature of 100 to 350 degree Celsius under a reaction pressure of 0.1 to 8 MPa at a WHSV for the compound having a lactone group of 0.1 to 15 $hour^{-1}$; step b2) is carried out at a reaction temperature of 160 to 400 degree Celsius under a reaction pressure of 0.1 to 8 MPa at a WHSV for the C4 olefin of 0.1 to 15 $hour^{-1}$; and step b1) or step c2) is carried out at a reaction temperature of 420 to 800 degree Celsius under a reaction pressure of 0.1 to 8 MPa at a WHSV for the C8 olefin of 0.3 to 10 $hour^{-1}$.

3. The process according to claim 1, wherein the compound selected from the group consisting of xylitol, glucose, cellobiose, cellulose, hemicellulose, and lignin is catalytically converted from a biomass selected from the group consisting of one or more of paper manufacture sludge, waste paper, bagasse, glucose, wood, corn cob, corn stover, and straw stover.

4. The process according to claim 1, wherein the acidic oxide is one or more selected from the group consisting of solid oxide of an element from Group IIIA of the periodic table of elements and solid oxide of an element from Group IVA of the periodic table, the oxide of bismuth is $Bi_2O_3$, and the strongly acidic cation exchange resin is one or more selected from the group consisting of macroporous sulfonic acidic cation exchange resin and halogen modified sulfonic acidic cation exchange resin.

5. The process according to claim 1, wherein the molecular sieve is one or more selected from the group consisting of ZSM-type molecular sieve, Y-type molecular sieve, beta-type molecular sieve, L-type molecular sieve, and MCM-type molecular sieve.

6. The process according to claim 5, wherein the molecular sieve is a molecular sieve composition, comprising the following components of m1), n1), and p1) or comprising the following components of m2) and n2), wherein:
- m1) is 20 to 80 parts by weight of the molecular sieve,
- n1) is 20 to 80 parts by weight of a binder,
- p1) 0 to 10 parts by weight of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce,
- m2) is 90 to 99.99 parts by weight of the molecular sieve, and
- p2) is 0.01 to 10 parts by weight of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce.

7. The process according to claim 1, wherein in step a1), the compound having a lactone group is contacted with catalyst bed layers containing the decarboxylation and dimerisation catalyst to produce a C8 olefin, the catalyst bed layers comprising at least two layers of the decarboxylation and dimerisation catalyst, wherein the acidities of any two adjacent layers of the decarboxylation and dimerisation catalysts are different.

8. The process according to claim 1, wherein the solid superacid is one or more selected from the group consisting of a supported Lewis acid superacid a composite inorganic metal salt/Lewis acid composite superacid, a sulfated metal oxide superacid.

9. The process according to claim 8, wherein the support of the supported Lewis acid superacid is one or more compounds selected from the group consisting of solid oxide of an element from Group IIIA and solid oxide of an element from Group IVA, of the periodic table,
the Lewis acid of the supported Lewis acid superacid is one or more selected from the group consisting of halide of an element from Group VB and halide of an element from Group VA of the periodic table of elements,
the inorganic metal salt of the composite superacid is one or more selected from the group consisting of inorganic acid salt of a metal element from Group IB, inorganic acid salt of a metal element from Group IIB, inorganic acid salt of a metal element from Group VII and inorganic acid salt of a metal element from Group VIII of the periodic table of elements,
the Lewis acid of the composite superacid is one or more selected from the group consisting of halide of an element from Group VB, halide of an element from Group IIIA and halide of an element from Group VA of the periodic table of elements,
the metal oxide of the sulfated metal oxide superacid is oxide A or oxide B, wherein oxide A is oxide of a metal element from Group IVB, wherein oxide B is obtained by modifying oxide A with one or more modifying elements selected from the group consisting of metal element from Group VIIB (in the form of oxide), noble metal element from Group VIII, base metal element from Group VIII, metal element from Group VIB, and lanthanide metal element of the periodic table of elements.

10. The process according to claim 9, wherein in the supported Lewis acid superacid, the Lewis acid is in an amount of 1 to 30 wt %, relative to the weight of the support,
in the composite superacid, the weight ratio between the inorganic metal salt and the Lewis acid is 1-30:100,
in the assulfated metal oxide superacid, the metal oxide has a sulfated rate of 0.5-25 wt %, and
in oxide B, the weight ratio of the modifying element in the form of oxide (calculated as oxide) to oxide A is 0.1-25:100, and the weight ratio of the modifying element in the form of metal elementary substance (calculated as metal) to the oxide A is 0.1-15:100.

11. The process according to claim 1, wherein the composite metal oxide is a composite of oxide C and oxide D, wherein oxide C is an oxide of a metal element from Group IVB, and oxide D is one or more selected from the group consisting of oxide of a metal element from Group IIIA of the periodic table of elements, oxide of a metal element from Group VII, oxide of a metal element from Group VIB and lanthanide metal element of the periodic table of elements.

12. The process according to claim 11, wherein the ratio of oxide C to oxide D is 60:40 to 99.9:0.1, calculated in parts by weight.

13. The process according to claim 1, further comprising a step of catalytic conversion of the biomass material, optionally followed by catalytic hydrogenation, so as to produce the compound having a lactone group.

14. A process for producing p-xylene, comprising the steps of:
producing aromatics according to claim 1; and
separating p-xylene from the aromatics.

15. A process for producing terephthalic acid, comprising the steps of:
producing p-xylene according to claim 14; and
converting the p-xylene into terephthalic acid.

16. The process according to claim 1, $R_1$ is 1,2-ethylidene and $R_2$ is selected from the group consisting of hydrogen and $C_{1-4}$ linear or branched alkyl.

17. The process according to claim 1, wherein step a1) is carried out at the reaction temperature of 160 to 300 degree Celsius under the reaction pressure of 0.1 to 4 MPa and at the WHSV for the compound having a lactone group of 0.6 to 5 hour$^{-1}$; step a2) is carried out at the reaction temperature of 120 to 250 degree Celsius under the reaction pressure of 0.1 to 4 MPa and at the WHSV for the compound having a lactone group of 0.6 to 5 hour$^{-1}$; step b2) is carried out at the reaction temperature of 160 to 300 degree Celsius under the reaction pressure of 0.1 to 4 MPa and at the WHSV for the C4 olefin of 0.6 to 5 hour$^{-1}$; and step b1) or step c2) is carried out at the reaction temperature of 450 to 550 degree Celsius under the reaction pressure of 0.1 to 4 MPa at the WHSV for the C8 olefin of 0.3 to 5 hour$^{-1}$.

18. The process according to claim 1, wherein the decarboxylation catalyst is one or more selected from the group consisting of strongly acidic cation exchange resin and solid superacid; the dimerisation catalyst is ZSM-5 or M/ZSM-5, wherein M is selected from the group consisting of Zn, Ga, Sn, and a combination thereof.

19. The process according to claim 1, wherein the acidic oxide is one or more selected from the group consisting of $Al_2O_3$, $Al_2O_3$-$SiO_2$, and $SiO_2$, the oxide of bismuth is $Bi_2O_3$.

20. The process according to claim 1, wherein the molecular sieve is one or more selected from the group consisting of ZSM-5, Y-type molecular sieve, beta-type molecular sieve, and MCM-41.

21. The process according to claim 6, wherein the binder is one or more selected from the group consisting of silica sol, pseudo-boehmite, alumina, acid treated clay, kaolin, montmorillonite, and bentonite.

22. The process according to claim 6, wherein the molecular sieve is a molecular sieve composition, comprising the components of m1), n1), and p1) or comprising the components of m2) and p2), wherein
- m1) is 50 to 80 parts by weight of the molecular sieve,
- n1) is 20 to 50 parts by weight of a binder selected from the group consisting of silica sol, pseudo-boehmite, alumina, acid treated clay, kaolin, montmorillonite, bentonite, and combinations thereof,
- p1) is 0.01 to 5 parts by weight of an auxiliary selected from the group consisting of Ca, K, Mg, Cr, Mo, Fe, Ni, Cu, Zn, Ga, Ru, Pd, Pt, Ag, B, Sn, P, La, Ce, and mixtures thereof,
- m2) is 95 to 99.99 parts by weight of the molecular sieve, and
- p2) is 0.01 to 5 parts by weight) of an auxiliary selected from the group consisting of Ca, K, Mg, Cr, Mo, Fe, Ni, Cu, Zn, Ga, Ru, Pd, Pt, Ag, B, Sn, P, La, Ce, and mixtures thereof.

23. The process according to claim 8, wherein the support of the Lewis acid supported solid superacid is one or more of selected from the group consisting of $SiO_2$, $B_2O_3$, and $Al_2O_3$,
- the Lewis acid of the supported Lewis acid superacid is one or more selected from the group consisting of $PF_3$, $AsF_3$, $SbF_3$, $BiF_3$, $SbF_5$, $TaF_3$, $VF_3$ and $NbF_3$,
- the inorganic metal salt of the solid of the composite superacid is one or more selected from the group consisting of haloid acid salt of a metal element from Group IB, haloid acid salt of a metal element from Group IIB, haloid acid salt of a metal element from Group VII, and haloid acid salt of a metal element from Group VIII of the periodic table of elements,
- the Lewis acid of the composite superacid is one or more selected from the group consisting of chloride of an element from Group VB, chloride of an element from Group IIIA, and chloride of an element from Group VA,
- in the the sulfated metal oxide superacid, oxide A of a metal element from $ZrO_2$, $TiO_2$, and the modifying element in oxide B is one or more selected from the group consisting of metal element from Group IIIA (in the form of oxide), metal element from Group VIIB (in the form of oxide), noble metal element from Group VIII (in the form of metal elementary substance), base metal element from Group VIII (in the form of oxide), metal element from Group VIB (in the form of oxide), and lanthanide metal element (in the form of oxide) of the periodic table of elements.

24. The process according to claim 1, wherein the solid superacid is one or more selected from the group consisting of $SbF_5/SiO_2$—$Al_2O_3$, $PF_3/Al_2O_3$—$B_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$—$B_2O_3$, $VF_3/Al_2O_3$—B203, $NbF_3/Al_2O_3$—$B_2O_3$,
$AlCl_3$—$CuCl_2$,
$SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$, $SO_4^{2-}/ZrO_2$—$Fe_2O_3$—$MnO_2$, W modified $SO_4^{2-}/Al_2O_3$—$ZrO_2$, and Mo modified $Sl_4^{2-}/Al_2O_3$—$ZrO_2$.

25. The process according to claim 9, wherein in the supported Lewis acid superacid, the Lewis acid is in an amount of 1 to 15 wt %, relative to the weight of the support,
- in the composite superacid, the weight ratio between the inorganic metal salt and the Lewis acid is 1-15:100,
- in the sulfated metal oxide superacid, the metal oxide has a sulfated rate of 1-8 wt %, and
- in oxide B, the weight ratio of the modifying element in the form of oxide (calculated as oxide) to oxide A is 0.5-10:100, and the weight ratio of the modifying element in the form of metal elementary substance (calculated as metal) to oxide A is 0.3-6:100.

26. The process according to claim 1, wherein the composite metal oxide is a composite oxide of $ZrO_2$ and one or more oxides D selected from the group consisting of $MnO_2$, $Mo_2O_3$, $WO_3$, $La_2O_3$, and $CeO_2$.

* * * * *